United States Patent
Stürmer et al.

(10) Patent No.: US 7,888,080 B2
(45) Date of Patent: Feb. 15, 2011

(54) ENZYMATIC REDUCTION FOR PRODUCING OPTICALLY ACTIVE ALCOHOLS

(75) Inventors: Rainer Stürmer, Rödersheim-Gronau (DE); Maria Keβeler, Mannheim (DE); Bernhard Hauer, Fuβgönheim (DE); Thomas Friedrich, Darmstadt (DE); Michael Breuer, Darmstadt (DE); Hartwig Schröder, Nuβloch (DE)

(73) Assignee: BASF SE, Ludwigshafen (DE)

( * ) Notice: Subject to any disclaimer, the term of this patent is extended or adjusted under 35 U.S.C. 154(b) by 0 days.

(21) Appl. No.: 12/158,390

(22) PCT Filed: Dec. 13, 2006

(86) PCT No.: PCT/EP2006/069680

§ 371 (c)(1),
(2), (4) Date: Jun. 20, 2008

(87) PCT Pub. No.: WO2007/074070

PCT Pub. Date: Jul. 5, 2007

(65) Prior Publication Data

US 2008/0318288 A1 Dec. 25, 2008

(30) Foreign Application Priority Data

Dec. 23, 2005 (DE) ........................ 10 2005 062 662

(51) Int. Cl.
C12P 17/00 (2006.01)
C12N 9/14 (2006.01)
(52) U.S. Cl. ........................................ 435/117; 435/195
(58) Field of Classification Search ........................ None
See application file for complete search history.

(56) References Cited

U.S. PATENT DOCUMENTS

| 5,362,886 A | 11/1994 | Berglund |
| 2006/0211099 A1 | 9/2006 | Althöfer et al. |
| 2007/0083055 A1 | 4/2007 | Sturmer et al. |

FOREIGN PATENT DOCUMENTS

| EP | 0273658 B1 | 7/1988 |
| EP | 0457559 A2 | 11/1991 |
| WO | WO-2004/090094 A2 | 10/2004 |
| WO | WO-2005/033094 A2 | 4/2005 |
| WO | WO-2005/108590 A2 | 11/2005 |

OTHER PUBLICATIONS

Chica et al. Curr Opin Biotechnol. Aug. 2005;16(4):378-84.*
Wheeler, W. J., et al., "An Asymmetirc Synthesis of Duloxetine Hydrochloride, A Mixed Uptake Inhibitor of Serotonin and Norepinephrine, and its C-14 Labeled Isotopomers", Journal of Labelled Compounds and Radiopharmaceuticals, 1994, vol. XXXVI, No. 3, pp. 213-223.
Itoh, N., et al., "Chiral Alcohol Production by NADH-Dependent Phenylacetaldehyde Reductase Coupled with in situ Regeneration of NADH", Eur, J. Biochem., 2002, vol. 269, pp, 2394-2402.
Korkhin, Y., et al., "NADP-dependent Bacterial Alcohol Dehydrogenases: Crystal Structure, Cofactor-Binding and Cofactor Specificity of the ADHs of *Clostridium beijerinckii* and *Thermoanaerobacter brockii*", J. Mol. Biol., vol. 278, (1998), pp. 967-981.

* cited by examiner

Primary Examiner—Delia M Ramirez
Assistant Examiner—Younus Meah
(74) *Attorney, Agent, or Firm*—Connolly Bove Lodge & Hutz LLP

(57) ABSTRACT

A process for preparing optically active alkanols of the formula I

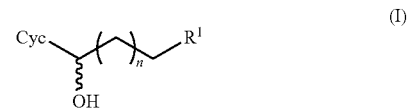

in which
n is an integer from 0 to 5;
Cyc is an optionally substituted, mono- or polynuclear, saturated or unsaturated, carbocyclic or heterocyclic ring, and
$R^1$ is halogen, SH, OH, $NO_2$, $NR^2R^3$ or $NR^2R^3R^{4+}X^-$, with $R^2$, $R^3$ and $R^4$ independently of one another being hydrogen or a lower alkyl or lower alkoxy radical and $X^-$ being a counterion,
which process comprises incubating in a medium comprising alkanone of the formula II

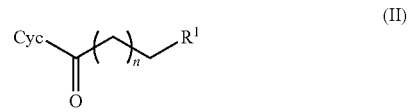

in which n, Cyc and $R^1$ are as defined above,
an enzyme having a polypeptide sequence
(i) SEQ ID NO: 1 or
(ii) in which, compared to SEQ ID NO:1, up to 25% of the amino acid radicals have been altered by deletion, insertion, substitution or a combination thereof and which retains at least 50% of the enzymic activity of SEQ ID NO:1,
with the compound of the formula II being enzymically reduced to give the compound of the formula I, and isolating the product formed.

10 Claims, No Drawings

ENZYMATIC REDUCTION FOR PRODUCING OPTICALLY ACTIVE ALCOHOLS

RELATED APPLICATIONS

This application is a national stage application under 35 U.S.C. §371 of PCT/EP2006/069680, filed Dec. 13, 2006, which is incorporated by reference in its entirety, and claims priority of German application 10 2005 062 662.9, filed Dec. 23, 2005, which is incorporated by reference in its entirety.

SEQUENCE LISTING SUBMISSION

The Sequence Listing associated with this application is filed in electronic format via EFS-Web and hereby incorporated by reference in its entirety into the specification. The name of the text file containing the Sequence Listing is SequenceList_12810_00706_US. The size of the text file is 8.84 KB, and the text file was created on Jun. 18, 2008.

The present invention relates to a process for preparing optically active alkanols by enzymically reducing the corresponding ketones, in particular to preparing (1S)-3-methylamino-1-(2-thienyl)propan-1-ol and (1S)-3-chloro-1-(2-thienyl)propan-1-ol.

BACKGROUND OF THE INVENTION (1S)-3-Methylamino-1-(2-thienyl)propan-1-ol ("Duloxetine alcohol") is a building block in Duloxetine synthesis. Duloxetine® is a drug which is currently at the approval stage and is intended to be used in the depression and incontinence fields of indication.

EP-B-0273658 describes a process for preparing the base corresponding to Duloxetine by reacting 2-acetylthiophene with formaldehyde and dimethylamine in a Mannich reaction, reducing the keto group of the Mannich base thus obtained to give the racemic (S)-3-N,N-dimethylamino-1-(thien-2-yl)propan-1-ol, etherifying the alcohol function with naphthyl fluoride and finally converting the dimethylamino group to a methylamino function. The desired naphthyl ether enantiomer is obtained using chiral starting materials or by resolution of the racemates at the stage of the final product, for example via the salts, using optically active acids or chromatography on a chiral stationary phase.

U.S. Pat. No. 5,362,886 describes an analogous process which comprises adding S-mandelic acid to the racemic propanol obtained after reduction of the keto group. The S enantiomer of the alcohol, obtained in this process, is used in the subsequent reaction stages.

EP-A-0457559 likewise describes a process analogous to that of EP-B-0273658. Here, the keto group of the Mannich base is reduced to the S-enantiomeric form of the alcohol by using the asymmetric reduction system LAH-lcb (lithium aluminum hydride [(2R,2S)-(−)-4-dimethylamino-1,2-diphenyl-3-methyl-2-butanol]). The disadvantage here, besides the costs, is the sensitivity of the LAH-lcb reduction system which is stable only for a few minutes.

W. J. Wheeler and F. Kuo describe in Journal of Labelled Compounds and Radiopharmaceuticals, Volume XXXVI, No, 3, pages 213 to 223, a process for preparing Duloxetine. To this end, thiophene-2-carbonyl chloride is reacted, in a Stille coupling, with vinyl tri-n-butylstannane in the presence of catalytic amounts of benzylchloro-bis(triphenylphosphine)palladium(II) in DMPU (dimethylpropyleneurea) to give 1-(thien-2-yl)propenone of the formula (V)

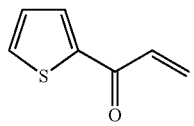

which is subsequently converted, by treatment with hydrogen chloride, into 3-chloro-1-(thien-2-yl)propan-1-one of the formula (VI)

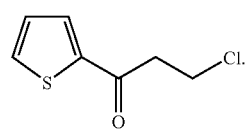

The chloropropanone obtained in this way is then reduced using a chiral oxazaborlidine and $BH_3$ to give (S)-3-chloro-1-(thien-2-yl)propan-1-ol of the formula (VII)

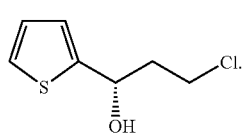

The alcohol obtained in this way is converted, by successively reacting with sodium iodide and subsequently with methylamine, into (S)-3-methylamino-1-(thien-2-yl)propan-1-ol. Subsequent successive reaction with sodium hydride, 1-fluoronaphthalene and hydrogen chloride produces Duloxetine in the form of the hydrochloride.

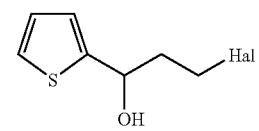

Hal=halogen

WO 05/108590 describes dehydrogenases for preparing optically active alkanols by reducing the corresponding alkanones, in particular preparing 3-methylamino-1-(2-thienyl)propanone and 3-chloro-1-(2-thienyl)propanone.

SUMMARY OF THE INVENTION

It was therefore the object of the invention to find a way of stereospecifically reducing substituted alkanones such as 3-methylamino-1-(2-thienyl)propanone and 3-chloro-1-(2-thienyl)propanone.

This object was achieved by the surprising finding that enzymes with dehydrogenase activity, which can be prepared from microorganisms of the genus *Lactobacillus*, in particular of the species *Lactobacillus brevis*, are capable of stereospecifically catalyzing the above reaction.

The present invention firstly relates to a process for preparing optically active alkanols of the formula I

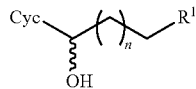

(I)

in which
n is an integer from 0 to 5, in particular 0, 1 or 2;
Cyc is an optionally substituted, mono- or polynuclear, saturated or unsaturated, carbocyclic or heterocyclic ring, in particular an optionally substituted, unsaturated, mononuclear heterocyclic ring, and
$R^1$ is halogen, SH, OH, $NO_2$, $NR^2R^3$ or $NR^2R^3R^{4+}X^-$, in particular halogen or $NR^2R^3$, with $R^2$, $R^3$ and $R^4$ independently of one another being hydrogen or a lower alkyl or lower alkoxy radical and $X^-$ being a counterion, which process comprises incubating in a medium comprising an alkanone of the formula II

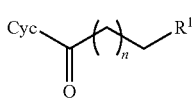

(II)

in which n, Cyc and $R^1$ are as defined above, an enzyme having a polypeptide sequence
(i) SEQ ID NO: 2 or
(ii) in which, compared to SEQ ID NO:2, up to 25% of the amino acid radicals have been altered by deletion, insertion, substitution or a combination thereof and which retains at least 50% of the enzymic activity of SEQ ID NO:2, with the compound of the formula II being enzymically reduced to give the compound of the formula I, and isolating the essentially enantiomerically pure product formed.

In a particularly preferred embodiment, the process serves to prepare derivatives of the 1-(2-thienyl)-(S)-propanol of the formula III

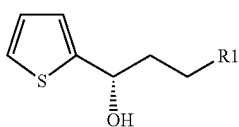

(III)

where $R^1$=Cl or $NHCH_3$,
wherein in a medium comprising a derivative of the 1-(2-thienyl)propanone of the formula IV

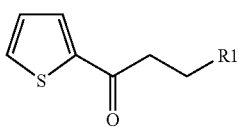

(IV)

this compound is enzymically reduced to give the compound of the formula III and the essentially enantiomerically pure product formed is isolated.

Preference is given to using in this process an enzyme with dehydrogenase activity, which may be prepared from microorganisms of the genera *Lactobacillus*.

Particular preference is given to using *Lactobacillus brevis* dehydrogenases.

In a particularly preferred embodiment of the process, the enzyme with dehydrogenase activity is selected from among enzymes which comprise an amino acid sequence according to SEQ ID NO: 1 or a sequence derived therefrom in which up to 25%, preferably up to 20%, particularly preferably up to 15%, in particular up to 10, 9, 8, 7, 6, 5, 4, 3, 2, 1%, of the amino acid residues have been altered by a deletion, a substitution, an insertion or a combination of deletion, substitution and insertion, with the polypeptide sequences altered compared to SEQ ID NO: 1 retaining at least 50%, preferably 65%, particularly preferably 80%, in particular more than 90%, of the enzymic activity of SEQ ID NO:1. In this connection, enzymic activity of SEQ ID NO:1 is intended to mean the ability to reduce the ketones of the formula (IV), where $R^1$=Cl, in an enantioselective manner to give the (S) alcohol having the general formula (III).

The process of the invention is preferably carried out with addition of reduction equivalents (NADH or NADPH) or under (biochemical or electrochemical) conditions regenerating the reduction equivalents consumed in the reaction. For these preferred embodiments reference is made to examples 5 and 6 which describe generally applicable regenerating systems.

Another suitable embodiment for cofactor regeneration in the process of the invention is the use of a water-immiscible oxidizable compound, for example a higher alcohol, preferably hexanol, which may be present in a second liquid phase in the reaction medium.

Further preference is given to reacting the compound of the general formula II, such as, for example, the formula IV, in the presence of a microorganism selected from among bacteria of the families Enterobacteriaceae, Pseudomonadaceae, Rhizobiaceae, Streptomycetaceae and Nocardiaceae. Said microorganism may be in particular a recombinant microorganism which has been transformed with a nucleic acid construct coding for an enzyme with dehydrogenase activity as defined above.

The invention relates in particular to
isolating or recombinantly preparing a microorganism producing an enzyme with dehydrogenase activity from a natural source,
propagating said microorganism,
isolating, if appropriate, said enzyme with dehydrogenase activity from said microorganism or preparing a protein fraction comprising said enzyme, and
transferring the microorganism according to stage b) or the enzyme according to stage c) to a medium comprising a compound of the formula I.

The invention relates to enzymes with dehydrogenase activity, having a polypeptide sequence
(i) SEQ ID NO: 1 or
(ii) in which, compared to SEQ ID NO:1, up to 25% of the amino acid radicals have been altered by deletion, insertion, substitution or a combination thereof and which retains at least 50% of the enzymic activity of SEQ ID NO:1.

The invention moreover relates to coding nucleic acid sequences comprising the sequence coding for a polypeptide as defined above.

The invention furthermore relates to expression cassettes comprising a coding nucleic acid sequence as defined above, which is operatively linked to at least one regulatory nucleic acid sequence.

The invention further relates to recombinant vectors comprising at least one such expression cassette.

The invention also relates to prokaryotic or eukaryotic hosts which have been transformed with at least one vector of the invention.

Finally, the invention relates to the use of an enzyme with dehydrogenase activity as defined above or of a microorganism producing said enzyme for preparing compounds of the formulae I or Ill, and to further processing thereof, for example for preparing duloxetine (formula VIII)

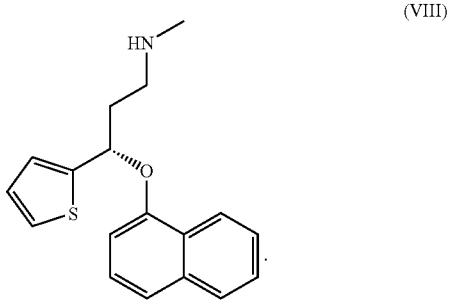

(VIII)

DETAILED DESCRIPTION OF THE INVENTION

A. General Terms and Definitions

Unless stated otherwise, the following general meanings apply:

"Halogen" is fluoro, chloro, bromo or iodo, in particular fluoro or chloro.

"Lower alkyl" are straight-chain or branched alkyl radicals 1 to 6 carbon atoms, such as methyl, ethyl, isopropyl or n-propyl, n-, iso-, sec- or tert-butyl, n-pentyl or 2-methylbutyl, n-hexyl, 2-methylpentyl, 3-methylpentyl, 2-ethylbutyl.

"Lower alkenyl" are the mono- or poly-, preferably mono- or di-, unsaturated analogs of the abovementioned alkyl radicals having 2 to 6 carbon atoms, it being possible for the double bond to be in any position of the carbon chain.

"Lower alkoxy" are the oxygen-terminated analogs of the alkyl radicals above.

"Aryl" is a mono- or polynuclear, preferably mono- or dinuclear, optionally substituted aromatic radical, in particular phenyl or naphthyl bound via any ring position, such as 1- or 2-naphthyl. These aryl radicals may, if appropriate, bear 1 or 2 identical or different substituents selected from among halogen, lower alkyl, lower alkoxy as defined above or trifluoromethyl.

Substituted alkanones, (S)-alkanols and derivatives thereof.

Alkanols accessible according to the invention by enzymic catalysis are those of the formula (I) above in which n is an integer from 0 to 5;

Cyc is an optionally substituted, mono- or polynuclear, saturated or unsaturated, carbocyclic or heterocyclic ring, and $R^1$ is halogen, SH, OH, $NO_2$, $NR^2R^3$ or $NR^2R^3R^{4+}X^-$, with $R^2$, $R^3$ and $R^4$ independently of one another being hydrogen or a lower alkyl or lower alkoxy radical and $X^-$ being a counterion.

The alkanones of the above formula II which are used for enzymic synthesis are compounds known per se and accessible by applying well-known organic syntheses (cf. e.g. EP-A-0 273 658).

In the compounds above, n is preferably 0, 1 or 2, in particular 1.

Examples of carbo- and heterocyclic groups Cyc, which may be mentioned, are in particular mono- or dinuclear, preferably mononuclear, groups having up to 4, preferably 1 or 2, identical or different ring heteroatoms selected from among O, N and S:

These carbo- or heterocyclic rings comprise in particular from 3 to 12, preferably 4, 5 or 6, ring carbon atoms. Examples which may be mentioned are cyclopropyl, cyclobutyl, cyclopentyl, cyclohexyl, cycloheptyl, the mono- or polyunsaturated analogs thereof, such as cyclobutenyl, cyclopentenyl, cyclohexenyl, cycloheptenyl, cyclohexadienyl, cycloheptadienyl; and also 5- to 7-membered saturated or mono- or polyunsaturated heterocyclic radicals having 1 to 4 heteroatoms selected from among O, N and S, it being possible for the heterocycle, if appropriate, to be fused to another heterocycle or carbocycle. Mention must in particular be made of heterocyclic radicals derived from pyrrolidine, tetrahydrofuran, piperidine, morpholine, pyrrole, furan, thiophene, pyrazole, imidazole, oxazole, thiazole, pyridine, pyran, pyrimidine, pyridazine, pyrazine, cumarone, indole and quinoline.

In this case, the radicals Cyc may be bound via any ring position, preferably via a ring carbon atom, to the alkanone or the alkanol.

Examples of suitable Cyc radicals are 2-thienyl, 3-thienyl; 2-furanyl, 3-furanyl; 2-pyridyl, 3-pyridyl or 4-pyridyl; 2-thiazolyl, 4-thiazolyl or 5-thiazolyl; 4-methyl-2-thienyl, 3-ethyl-2-thienyl, 2-methyl-3-thienyl, 4-propyl-3-thienyl, 5-n-butyl-2-thienyl, 4-methyl-3-thienyl, 3-methyl-2-thienyl; 3-chloro-2-thienyl, 4-bromo-3-thienyl, 2-iodo-3-thienyl, 5-iodo-3-thienyl, 4-fluoro-2-thienyl, 2-bromo-3-thienyl, and 4-chloro-2-thienyl.

The radicals Cyc may furthermore be mono- or poly-, such as, for example, mono- or di-, substituted. The substituents are preferably located on a ring carbon atom. Examples of suitable substituents are halogen, lower alkyl, lower alkenyl, lower alkoxy, —OH, —SH, —$NO_2$ or $NR^2R^3$, where $R^2$ and $R^3$ are as defined above, preferably halogen or lower alkyl.

$R^1$ is in particular halogen, $NR^2R^3$ or $NR^2R^3R^{4+}X^-$, where $R^2$, $R^3$ and, respectively, $R^2$, $R^3$ and $R^4$ are independently of one another hydrogen or a lower alkyl or lower alkoxy radical and $X^-$ is a counterion, preference being given to one of the radicals $R^2$, $R^3$ and $R^4$ being hydrogen. Examples of suitable counterions are acid anions, as are produced, for example, when preparing an acid addition salt. Examples thereof are mentioned, for example, in EP-A-0 273 658 to which reference is made hereby. Preferred examples of radicals $R^1$ are in particular fluoro or chloro, and $NR^2R^3$ in which $R^2$ and $R^3$ are identical or different and are hydrogen or methyl, ethyl or n-propyl; $R^1$ is particularly preferably chloro or —NHmethyl.

C. Suitable Enzymes with Dehydrogenase Activity

Preferred enzymes with dehydrogenase activity comprise an amino acid sequence according to SEQ ID NO: 1.

The invention likewise comprises "functional equivalents" of the specifically disclosed enzymes with dehydrogenase activity and the use of these in the processes of the invention.

Within the context of the present invention, "functional equivalents" or analogs of the specifically disclosed enzymes are polypeptides which differ from these enzymes but which still possess the desired biological activity such as substrate specificity, for example. Thus, "functional equivalents" mean, for example, enzymes which reduce 3-chloro-1-(thien-2-yl)propan-1-one to the corresponding S alcohol and which have at least 50%, preferably 60%, particularly preferably 75%, very particularly preferably 90%, of the activity of an enzyme having the amino acid sequence listed in SEQ ID NO:1. Functional equivalents are also preferably stable between pH 4 to 10 and advantageously possess a pH optimum between pH 5 and 8 and also a temperature optimum in the range from 20° C. to 80° C.

According to the invention, "functional equivalents" also mean, in particular, mutants which have an amino acid other than the specifically mentioned amino acid in at least one sequence position of the abovementioned amino acid sequences but nevertheless possess one of the abovementioned biological activities. "Functional equivalents" thus comprise the mutants obtainable by one or more amino acid additions, amino acid substitutions, amino acid deletions and/or amino acid inversions, it being possible for said alterations to occur in any sequence position as long as they result in a mutant having the property profile of the invention. Functional equivalence also exists, in particular, when the reactivity patterns of the mutant and the unaltered polypeptide agree qualitatively, i.e. the same substrates are, for example, converted at different rates.

Examples of suitable amino acid substitutions can be found in the following table:

| Original residue | Substitution examples |
| --- | --- |
| Ala | Ser |
| Arg | Lys |
| Asn | Gln; His |
| Asp | Glu |
| Cys | Ser |
| Gln | Asn |
| Glu | Asp |
| Gly | Pro |
| His | Asn; Gln |
| Ile | Leu; Val |
| Leu | Ile; Val |
| Lys | Arg; Gln; Glu |
| Met | Leu; Ile |
| Phe | Met; Leu; Tyr |
| Ser | Thr |
| Thr | Ser |
| Trp | Tyr |
| Tyr | Trp; Phe |
| Val | Ile; Leu |

According to the invention, "functional equivalents" also mean, in particular, mutants which have an amino acid other than the specifically mentioned amino acid in at least one sequence position of the abovementioned amino acid sequences but nevertheless possess one of the abovementioned biological activities. "Functional equivalents" thus comprise the mutants obtainable by one or more amino acid additions, amino acid substitutions, amino acid deletions and/or amino acid inversions, it being possible for said alterations to occur in any sequence position as long as they result in a mutant having the property profile of the invention. Functional equivalence also exists, in particular, when the reactivity patterns of the mutant and the unaltered polypeptide agree qualitatively, i.e. the same substrates are, for example, converted at different rates.

"Functional equivalents" in the above sense are also "precursors" of the polypeptides described and also "functional derivatives" and "salts" of said polypeptides.

In this context, "precursors" are natural or synthetic precursors of the polypeptides with or without the desired biological activity.

The expression "salts" means both salts of carboxyl groups and acid addition salts of amino groups of the protein molecules of the invention. Salts of carboxyl groups can be prepared in a manner known per se and comprise inorganic salts such as sodium, calcium, ammonium, iron and zinc salts as well as salts with organic bases, for example amines, such as triethanolamine, arginine, lysine, piperidine and the like. The invention likewise relates to acid addition salts, for example salts with mineral acids such as hydrochloric acid or sulfuric acid and salts with organic acids such as acetic acid and oxalic acid.

"Functional derivatives" of polypeptides of the invention may likewise be prepared with the aid of known techniques at functional amino acid side groups or at their N-terminal or C-terminal ends. Derivatives of this kind comprise, for example, aliphatic esters of carboxylic acid groups, amides of carboxylic acid groups, which amides are obtainable by reacting with ammonia or with a primary or secondary amine; N-acyl derivatives of free amino groups, which derivatives are prepared by reacting with acyl groups; or O-acyl derivatives of free hydroxyl groups, which derivatives are prepared by reacting with acyl groups.

"Functional equivalents" naturally also comprise polypeptides which are available from other organisms and also naturally occurring variants. For example, areas of homologous sequence regions can be established by sequence comparison and equivalent enzymes can be determined on the basis of the specific guidelines of the invention.

"Functional equivalents" likewise comprise fragments, preferably individual domains or sequence motifs, of the polypeptides of the invention, which fragments have, for example, the desired biological function.

"Functional equivalents" are moreover fusion proteins which contain any of the abovementioned polypeptide sequences or functional equivalents derived therefrom and at least one further heterologous sequence which is functionally different therefrom and is functionally linked N-terminally or C-terminally (i.e. without any substantial reciprocal functional impairment of the fusion protein moieties). Nonlimiting examples of such heterologous sequences are signal peptides or enzymes, for example.

"Functional equivalents" which are comprised in the invention are homologs of the specifically disclosed proteins. Said homologs possess at least 60%, preferably at least 75%, in particular at least 85%, such as 90%, 95% or 99%, homology with one of the specifically disclosed amino acid sequences, as calculated using the algorithm of Pearson and Lipman, Proc. Natl. Acad, Sci. (USA) 85(8), 1988, 2444-2448. A percentage homology of a homologous polypeptide of the invention is in particular the percentage identity of the amino acid residues, based on the total length of any of the amino acid sequences specifically described herein.

In the case of a possible protein glycosylation, "functional equivalents" of the invention comprise proteins of the above-described type in deglycosylated or glycosylated form and also modified forms which can be obtained by altering the glycosylation pattern. Homologs of the proteins or polypeptides of the invention may be generated by mutagenesis, for example by point mutation or truncation of the protein.

Homologs of the proteins of the invention may be identified by screening combinatorial libraries of mutants such as truncation mutants, for example. For example, a variegated library of protein variants may be generated by combinatorial mutagenesis at the nucleic acid level, for example by enzymically ligating a mixture of synthetic oligonucleotides.

There are a large number of methods which may be used for preparing libraries of potential homologs from a degenerate oligonucleotide sequence. A degenerate gene sequence may be synthesized chemically in a DNA synthesizer and the synthetic gene may then be ligated into a suitable expression vector. Using a degenerate set of genes makes it possible to prepare all the sequences in a mixture which encode the desired set of potential protein sequences. Processes for synthesizing degenerate oligonucleotides are known to the skilled worker (e.g. Narang, S. A. (1983) Tetrahedron 39:3; Itakura et al. (1984) Annu. Rev. Biochem. 53:323; Itakura et al., (1984) Science 198:1056; Ike et al. (1983) Nucleic Acids Res. 11:477).

A plurality of techniques for screening gene products of combinatorial libraries which have been prepared by point mutations or truncation and for screening cDNA libraries for gene products having a selected property are known in the prior art. These techniques can be adapted for rapidly screening the gene libraries which have been generated by combinatorial mutagenesis of homologs of the invention. The most frequently employed techniques for screening large gene libraries which are subject to high-throughput analysis comprise cloning the gene library into replicable expression vectors, transforming the appropriate cells with the resulting vector library and expressing the combinatorial genes under conditions under which detection of the desired activity facilitates isolation of the vector which encodes the gene whose product was detected. Recursive ensemble mutagenesis (REM), a technique which increases the frequency of functional mutants in the libraries, may be used in combination with the screening tests in order to identify homologs (Arkin and Yourvan (1992) PNAS 89:7811-7815; Delgrave et al. (1993) Protein Engineering 6(3):327-331).

D. Nucleic Acid Sequences Coding for the Dehydrogenases

The invention relates in particular to nucleic acid sequences (single- and double-stranded DNA and RNA sequences, such as cDNA and mRNA, for example) which code for an enzyme with dehydrogenase activity of the invention. Preference is given to nucleic acid sequences which code, for example, for amino acid sequences according to SEQ ID NO:1 or for characteristic partial sequences thereof. The corresponding nucleic acids can readily be determined by back-translating SEQ ID NO:1 according to the genetic code. Preference is also given to adapting the nucleic acid sequence to the codon usage of the intended host organism in which said nucleic acid is to be expressed.

All of the nucleic acid sequences mentioned herein can be prepared in a manner known per se by chemical synthesis from the nucleotide building blocks, for example by means of fragment condensation of individual overlapping, complementary nucleic acid building blocks of the double helix. Oligonucleotides may, for example, be synthesized chemically, in a known manner, using the phosphoamidite method (Voet, Voet, 2nd edition, Wiley Press New York, pages 896-897). The assembly of synthetic oligonucleotides and filling-in of gaps with the aid of the DNA polymerase Klenow fragment and ligation reactions and also general cloning methods are described in Sambrook et al. (1989), Molecular Cloning: A laboratory manual, Cold Spring Harbor Laboratory Press.

The invention also relates to nucleic acid sequences (single- and double-stranded DNA and RNA sequences, such as cDNA and mRNA, for example) which code for any of the above polypeptides and their functional equivalents which are accessible by using artificial nucleotide analogs, for example.

The invention relates both to isolated nucleic acid molecules which code for polypeptides or proteins of the invention or for biologically active sections thereof and to nucleic acid fragments which may be used, for example, as hybridization probes or primers for identifying or amplifying coding nucleic acids of the invention.

The nucleic acid molecules of the invention may moreover comprise untranslated sequences from the 3' and/or the 5' end of the coding gene region.

The invention furthermore comprises the nucleic acid molecules complementary to the specifically described nucleotide sequences, or a section thereof.

The nucleotide sequences of the invention make it possible to generate probes and primers which can be used for identifying and/or cloning homologous sequences in other cell types and organisms. Probes and primers of this kind usually comprise a nucleotide sequence region which hybridizes, under "stringent" conditions (see below), to at least about 12, preferably at least about 25, such as, for example, about 40, 50 or 75, consecutive nucleotides of a sense strand of a nucleic acid sequence of the invention or of a corresponding antisense strand.

An "isolated" nucleic acid molecule is removed from other nucleic acid molecules which are present in the natural source of the nucleic acid and may moreover be essentially free of other cellular material or culture medium when it is prepared by means of recombinant techniques or free of chemical precursors or other chemicals when it is synthesized chemically.

A nucleic acid molecule of the invention may be isolated by means of standard molecular-biological techniques and the sequence information which is provided according to the invention. For example, cDNA may be isolated from a suitable cDNA library by using one of the specifically disclosed complete sequences or a section thereof as hybridization probe and using standard hybridization techniques (as described, for example, in Sambrook, J., Fritsch, E. F. and Maniatis, T. Molecular Cloning: A Laboratory Manual. 2nd edition, Cold Spring Harbor Laboratory, Cold Spring Harbor Laboratory Press, Cold Spring Harbor, N.Y., 1989). In addition, a nucleic acid molecule comprising any of the disclosed sequences or a section thereof can be isolated by polymerase chain reaction using the oligonucleotide primers which have been constructed on the basis of this sequence. The nucleic acid amplified in this way may be cloned into a suitable vector and characterized by DNA sequence analysis. The oligonucleotides of the invention may also be prepared by standard synthesis using, for example, an automatic DNA synthesizer.

The nucleic acid sequences of the invention can be identified and isolated in principle from any organisms of the genus *Lactobacillus*, in particular from *Lactobacillus brevis*. Nucleic acid sequences of the invention can, for example, be isolated from other organisms by using customary hybridization methods or the PCR technique, for example by way of genomic or cDNA libraries. These DNA sequences hybridize with the sequences of the invention under standard conditions. Use is advantageously made, for the hybridization, of short oligonucleotides of the conserved regions, for example from the active site, which conserved regions may be identified in a manner known to the skilled worker by way of comparisons with a dehydrogenase of the invention. However, it is also possible to use longer fragments of the nucleic acids of the invention or the complete sequences for the hybridization. Said standard conditions vary depending on the nucleic acid employed (oligonucleotide, longer fragment or complete sequence) or depending on which nucleic acid type, DNA or RNA, is used for the hybridization. Thus, for example, the melting temperatures for DNA:DNA hybrids are approx. 10° C. lower than those for DNA:RNA hybrids of the same length.

Depending on the nucleic acid, standard conditions mean, for example, temperatures between 42 and 58° C. in an aqueous buffer solution having a concentration of between 0.1 to 5×SSC (1×SSC=0.15 M NaCl, 15 mM sodium citrate, pH 7.2) or additionally in the presence of 50% formamide, such as, for example, 42° C. in 5×SSC, 50% formamide. Advantageously, the hybridization conditions for DNA:DNA hybrids are 0.1×SSC and temperatures between about 20° C. to 45° C., preferably between about 30° C. to 45° C. For DNA:RNA hybrids, the hybridization conditions are advantageously 0.1×SSC and temperatures between about 30° C. to 55° C., preferably between about 45° C. to 55° C. The temperatures indicated for the hybridization are melting temperature values which have been calculated by way of example for a nucleic acid having a length of approx. 100 nucleotides and a G+C content of 50% in the absence of formamide. The experimental conditions for the DNA hybridization are described in specialist textbooks of genetics, such as, for example, Sambrook et al., "Molecular Cloning", Cold Spring Harbor Laboratory, 1989, and can be calculated using formulae known to the skilled worker, for example as a function of the length of the nucleic acids, the type of hybrids or the G+C content. The skilled worker can obtain further information with regard to hybridization from the following textbooks: Ausubel et al. (eds), 1985, Current Protocols in Molecular Biology, John Wiley & Sons, New York; Hames and Higgins (eds), 1985, Nucleic Acids Hybridization: A Practical Approach, IRL Press at Oxford University Press, Oxford; Brown (ed), 1991, Essential Molecular Biology. A Practical Approach, IRL Press at Oxford University Press, Oxford.

The invention also relates to derivatives of the specifically disclosed or derivable nucleic acid sequences.

The invention also comprises those nucleic acid sequences which comprise "silent" mutations or have been altered, as compared with a specifically mentioned sequence, according to the codon usage of a specific source organism or host organism, as well as naturally occurring variants thereof, such as splice variants or allele variants, for example.

The invention also relates to sequences obtainable by way of conservative nucleotide substitutions (i.e. the amino acid in question is replaced with an amino acid of the same charge, size, polarity and/or solubility).

The invention also relates to the molecules which are derived from the specifically disclosed nucleic acids by way of sequence polymorphisms. These genetic polymorphisms can exist between individuals within a population as a result of natural variation. These natural variations usually give rise to a variance of from 1 to 5% in the nucleotide sequence of a gene.

Derivatives of a nucleic acid sequence of the invention mean, for example, allele variants which, at the deduced amino acid level, are at least 40%, preferably at least 60%, very particularly preferably at least 80, 85, 90, 93, 95 or 98%, homologous over the entire sequence region (with respect to homology at the amino acid level, the reader may refer to the above comments regarding the polypeptides). Advantageously, the homologies may be higher across subregions of the sequences.

Furthermore, derivatives also mean homologs of the nucleic acid sequences of the invention, for example fungal or bacterial homologs, truncated sequences, single-stranded DNA or RNA of the coding and noncoding DNA sequence.

Thus are, for example at the DNA level, at least 40%, preferably at least 60%, particularly preferably at least 70%, very particularly preferably at least 80%, homologous across the entire DNA region indicated.

Moreover, derivatives mean fusions with promoters, for example. The promoters which are located upstream of the nucleotide sequences indicated may have been altered by one or more nucleotide replacements, insertions, inversions and/or deletions without, however, the functionality and efficacy of the promoters being impaired. Furthermore, the efficacy of said promoters may be increased by altering their sequence or the promoters may be completely replaced with more active promoters, including those from organisms of other species.

Derivatives also mean variants whose nucleotide sequence in the region from −1 to −1000 bases upstream of the start codon or from 0 to 1000 bases downstream of the stop codon has been altered so as to after, preferably increase, gene expression and/or protein expression.

The invention furthermore comprises nucleic acid sequences which hybridize with coding sequences mentioned above under "stringent conditions". These polynucleotides can be found by screening genomic or cDNA libraries and, if appropriate, amplified therefrom by means of PCR using suitable primers and then isolated using suitable probes, for example. In addition, polynucleotides of the invention may also be synthesized chemically. This property means the ability of a polynucleotide or oligonucleotide to bind to a virtually complementary sequence under stringent conditions while, under these conditions, unspecific bonds between non-complementary partners are not formed. For this purpose, the sequences should be 70-100%, preferably 90-100%, complementary. The property of complementary sequences of being able to bind specifically to one another is utilized, for example, in the Northern or Southern blot technique or for primer binding in PCR or RT-PCR. Oligonucleotides of at least 30 base pairs in length are usually used for this purpose. In the Northern blot technique, for example, stringent conditions mean the use of a washing solution of 50-70° C., preferably 60-65° C., for example 0.1×SSC buffer containing 0.1% SDS (20×SSC: 3M NaCl, 0.3M sodium citrate, pH 7.0), for eluting unspecifically hybridized cDNA probes or oligonucleotides. As mentioned above, the only nucleic acids to remain bound to one another here are those which are highly complementary. The establishment of stringent conditions is known to the skilled worker and is described, for example, in Ausubel et al., Current Protocols in Molecular Biology, John Wiley & Sons, N.Y. (1989), 6.3.1-6.3.6.

E. Embodiments of Constructs of the Invention

The invention moreover relates to expression constructs comprising, under the genetic control of regulatory nucleic acid sequences, a nucleic acid sequence coding for a polypeptide of the invention; and also to vectors comprising at least one of these expression constructs.

Such constructs of the invention preferably comprise a promoter 5'-upstream of the particular coding sequence and a terminator sequence 3'-downstream and also, if appropriate, further customary regulatory elements which are in each case operatively linked to the coding sequence.

An "operative linkage" means the sequential arrangement of promoter, coding sequence, terminator and, if appropriate, further regulatory elements in such a way that each of the regulatory elements is able to fulfill its function as required in expressing the coding sequence. Examples of operatively Sinkable sequences are targeting sequences and also enhancers, polyadenylation signals and the like. Other regulatory elements comprise selectable markers, amplification signals, origins of replication and the like. Suitable regulatory sequences are described, for example, in Goeddel, Gene Expression Technology Methods in Enzymology 185, Academic Press, San Diego, Calif. (1990).

A nucleic acid construct of the invention means in particular those in which the gene for a dehydrogenase of the invention has been operatively or functionally linked to one or more regulatory signals for the purpose of regulating, e.g. increasing, expression of the gene.

In addition to these regulatory sequences, the natural regulation of these sequences may still be present upstream of the actual structural genes and, if appropriate, may have been genetically altered in such a way that the natural regulation has been switched off and expression of the genes has been increased. However, the nucleic acid construct may also have a simpler design, i.e. no additional regulatory signals have been inserted upstream of the coding sequence and the natural promoter, together with its regulation, has not been removed. Instead of this, the natural regulatory sequence is mutated in such a way that there is no longer any regulation and expression of the gene is increased.

A preferred nucleic acid construct also advantageously comprises one or more of the previously mentioned enhancer sequences which are functionally linked to the promoter and which enable expression of the nucleic acid sequence to be increased. Additional advantageous sequences such as further regulatory elements or terminators may also be inserted at the 3' end of the DNA sequences. The nucleic acids of the invention may be present in the construct in the form of one or more copies. The construct may also comprise additional markers such as antibiotic resistances or auxotrophy-complementing genes, if appropriate for the purpose of selecting said construct.

Regulatory sequences which are advantageous for the process of the invention are present, for example, in promoters such as the cos, tac, trp, tet, trp-tet, lpp, lac, lpp-lac, lacI$^q$, T7, T5, T3, gal, trc, ara, rhaP (rhaP$_{BAD}$)SP6, lambda-P$_R$ or lambda-P$_L$ promoter, which promoters are advantageously used in Gram-negative bacteria. Further advantageous regulatory sequences are present, for example, in the Gram-positive promoters amy and SPO2, in the yeast or fungal promoters ADC1, MFalpha, AC, P-60, CYC1, GAPDH, TEF, rp28, ADH. The pyruvate decarboxylase and methanoloxidase promoters, for example from *Hansenula*, are also advantageous in this connection. It is also possible to use artificial promoters for regulation.

For the purpose of expression in a host organism, the nucleic acid construct is advantageously inserted into a vector such as a plasmid or a phage, for example, which enables the genes to be expressed optimally in the host. Vectors mean, in addition to plasmids and phages, also any other vectors known to the skilled worker, i.e., for example, viruses such as SV40, CMV, baculovirus and adenovirus, transposons, IS elements, phasmids, cosmids, and linear or circular DNA. These vectors may be replicated autonomously in the host organism or replicated chromosomally. These vectors constitute a further embodiment of the invention. Examples of suitable plasmids are pLG338, pACYC184, pBR322, pUC18, pUC19, pKC30, pRep4, pHS1, pKK223-3, pDHE19.2, pHS2, pPLc236, pMBL24, pLG200, pUR290, pIN-III[113]-B1, lgt11 or pBdCl, in *E. coli*, pIJ101, pIJ364, pIJ702 or pIJ361, in *Streptomyces*, pUB110, pC194 or pBD214, in *Bacillus*, pSA77 or pAJ667, in *Corynebacterium*, pALS1, pIL2 or pBB116, in fungi, 2alphaM, pAG-1, YEp6, YEp13 or pEMBLYe23, in yeasts, or pLGV23, pGHlac$^+$, pBIN19, pAK2004 or pDH51, in plants. Said plasmids are a small selection of the possible plasmids. Other plasmids are well known to the skilled worker and can be found, for example, in the book Cloning Vectors (Eds. Pouwels P. H. et al. Elsevier, Amsterdam-New York-Oxford, 1985, ISBN 0 444 904018).

For the purpose of expressing the other genes which are present, the nucleic acid construct advantageously also comprises 3'-terminal and/or 5'-terminal regulatory sequences for increasing expression, which are selected for optimal expression in dependence on the host organism selected and the gene or genes.

These regulatory sequences are intended to enable the genes and protein expression to be specifically expressed. Depending on the host organism, this may mean, for example, that the gene is expressed or overexpressed only after induction or that it is expressed and/or overexpressed immediately.

In this connection, the regulatory sequences or factors may preferably influence positively and thereby increase expression of the genes which have been introduced. Thus, the regulatory elements may advantageously be enhanced at the level of transcription by using strong transcription signals such as promoters and/or enhancers. However, in addition to this, it is also possible to enhance translation by improving the stability of the mRNA, for example.

In a further embodiment of the vector, the vector which comprises the nucleic acid construct of the invention or the nucleic acid of the invention may also advantageously be introduced into the microorganisms in the form of a linear DNA and be integrated into the genome of the host organism by way of heterologous or homologous recombination. This linear DNA may consist of a linearized vector such as a plasmid or only of the nucleic acid construct or the nucleic acid of the invention.

In order to be able to express heterologous genes optimally in organisms, it is advantageous to alter the nucleic acid sequences in accordance with the specific codon usage employed in the organism. The codon usage can readily be determined with the aid of computer analyses of other known genes from the organism in question.

An expression cassette of the invention is prepared by fusing a suitable promoter to a suitable coding nucleotide sequence and to a terminator signal or polyadenylation signal. Common recombination and cloning techniques, as are described, for example, in T. Maniatis, E. F. Fritsch and J. Sambrook, Molecular Cloning: A Laboratory Manual, Cold Spring Harbor Laboratory, Cold Spring Harbor, N.Y. (1989) and also in T. J. Silhavy, M. L. Berman and L. W. Enquist, Experiments with Gene Fusions, Cold Spring Harbor Laboratory, Cold Spring Harbor, N.Y. (1984) and in Ausubel, F. M, et al., Current Protocols in Molecular Biology, Greene Publishing Assoc. and Wiley Interscience (1987) are used for this purpose.

In order to achieve expression in a suitable host organism, the recombinant nucleic acid construct or gene construct is advantageously inserted into a host-specific vector which enables the genes to be expressed optimally in the host. Vectors are well known to the skilled worker and may be found, for example, in "Cloning Vectors" (Pouwels P. H. et al., Eds., Elsevier, Amsterdam-New York-Oxford, 1985).

F. Host Organisms Useful According to the Invention

It is possible to prepare, with the aid of the vectors or constructs of the invention, recombinant microorganisms which are, for example, transformed with at least one vector of the invention and which may be used for producing the polypeptides of the invention. Advantageously, the above-described recombinant constructs of the invention are introduced into a suitable host system and expressed. In this connection, familiar cloning and transfection methods known to the skilled worker, such as, for example, coprecipitation, protoplast fusion, electroporation, retroviral transfection and the like, are preferably used in order to cause said nucleic acids to be expressed in the particular expression system. Suitable systems are described, for example, in Current Protocols in Molecular Biology, F. Ausubel et al., Eds., Wiley Interscience, New York 1997, or Sambrook et al. Molecular Cloning: A Laboratory Manual. 2nd edition, Cold Spring Harbor Laboratory, Cold Spring Harbor Laboratory Press, Cold Spring Harbor, N.Y., 1989.

According to the invention, it is also possible to prepare homologously recombined microorganisms. For this purpose, a vector which comprises at least one section of a gene of the invention or of a coding sequence in which, if appropriate, at least one amino acid deletion, amino acid addition or amino acid substitution has been introduced in order to modify, for example functionally disrupt, the sequence of the invention (knock out vector), is prepared. The introduced sequence may also be a homolog from a related microorganism or be derived from a mammalian, yeast or insect source, for example. Alternatively, the vector used for homologous recombination may be designed in such a way that the endogenous gene is, in the case of homologous recombination, mutated or otherwise altered but still encodes the functional protein (e.g. the upstream regulatory region may have been altered in such a way that expression of the endogenous protein is thereby altered). The altered section of the gene of the invention is in the homologous recombination vector. The construction of vectors which are suitable for homologous recombination is described, for example, in Thomas, K. R. and Capecchi, M. R. (1987) Cell 51:503.

Recombinant host organisms suitable for the nucleic acid of the invention or the nucleic acid construct are in principle any prokaryotic or eukaryotic organisms. Advantageously, microorganisms such as bacteria, fungi or yeasts are used as host organisms. Gram-positive or gram-negative bacteria, preferably bacteria of the families Enterobacteriaceae, Pseudomonadaceae, Rhizobiaceae, Streptomycetaceae or Nocardiaceae, particularly preferably bacteria of the genera *Escherichia, Pseudomonas, Streptomyces, Nocardia, Burkholderia, Salmonella, Agrobacterium* or *Rhodococcus*, are advantageously used. Very particular preference is given to the genus and species *Escherichia coli*. In addition, further advantageous bacteria can be found in the group of the alpha-proteobacteria, beta-proteobacteria or gamma-proteobacteria.

In this connection, the host organism or host organisms of the invention comprise preferably at least one of the nucleic acid sequences, nucleic acid constructs or vectors which are described in this invention and which encode an enzyme with dehydrogenase activity of the invention.

The organisms used in the process of the invention are, depending on the host organism, grown or cultured in a manner known to the skilled worker. Microorganisms are usually grown in a liquid medium which comprises a carbon source, usually in the form of sugars, a nitrogen source, usually in the form of organic nitrogen sources such as yeast extract or salts such as ammonium sulfate, trace elements such as iron salts, manganese salts, magnesium salts and, if appropriate, vitamins, at temperatures of between 0° C. and 100° C., preferably between 10° C. and 60° C., while being gassed with oxygen. In this connection, the pH of the nutrient liquid may be kept at a fixed value, i.e. may or may not be regulated during cultivation. The cultivation may be carried out batchwise, semibatchwise or continuously. Nutrients may be introduced at the beginning of the fermentation or be fed in subsequently in a semicontinuous or continuous manner. The ketone may be added directly to the culture or, advantageously, after cultivation. The enzymes may be isolated from the organisms by using the method described in the examples or be used for the reaction as a crude extract.

G. Recombinant Preparation of the Polypeptides of the Invention

The invention furthermore relates to processes for recombinantly preparing polypeptides of the invention or functional, biologically active fragments thereof, with a polypeptide-producing microorganism being cultured, if appropriate expression of the polypeptides being induced and said polypeptides being isolated from the culture. The polypeptides may also be produced in this way on an industrial scale if this is desired.

The recombinant microorganism may be cultured and fermented by known methods. Bacteria may, for example, be propagated in TB medium or LB medium and at a temperature of from 20 to 40° C. and a pH of from 6 to 9. Suitable culturing conditions are described in detail, for example, in T. Maniatis, E. F. Fritsch and J. Sambrook, Molecular Cloning: A Laboratory Manual, Cold Spring Harbor Laboratory, Cold Spring Harbor, N.Y. (1989).

If the polypeptides are not secreted into the culture medium, the cells are then disrupted and the product is obtained from the lysate by known protein isolation methods. The cells may be disrupted, as desired, by means of high-frequency ultrasound, by means of high pressure, as, for example, in a French pressure cell, by means of osmolysis, by the action of detergents, lytic enzymes or organic solvents, by using homogenizers or by a combination of two or more of the methods listed.

The polypeptides may be purified using known chromatographic methods such as molecular sieve chromatography (gel filtration), for example Q Sepharose chromatography, ion exchange chromatography and hydrophobic chromatography, and also using other customary methods such as ultrafiltration, crystallization, salting-out, dialysis and native gel electrophoresis. Suitable methods are described, for example, in Cooper, F. G., Biochemische Arbeitsmethoden [original title: The tools of biochemistry], Verlag Walter de Gruyter, Berlin, New York or in Scopes, R., Protein Purification, Springer Verlag, New York, Heidelberg, Berlin.

It may be advantageous to isolate the recombinant protein by using vector systems or oligonucleotides which extend the cDNA by particular nucleotide sequences and thereby code for altered polypeptides or fusion proteins which are used, for example, to simplify purification. Examples of suitable modifications of this kind are "tags" acting as anchors, such as the modification known as the hexa-histidine anchor, or epitopes which can be recognized as antigens by antibodies (described, for example, in Harlow, E. and Lane, D., 1988, Antibodies: A Laboratory Manual. Cold Spring Harbor (N.Y.) Press). These anchors may be used for attaching the proteins to a solid support such as a polymer matrix, for example, which may, for example, be packed into a chromatography column, or to a microtiter plate or to another support.

At the same time, these anchors may also be used for identifying the proteins. The proteins may also be identified by using customary markers such as fluorescent dyes, enzyme markers which, after reaction with a substrate, form a detectable reaction product, or radioactive markers, either on their own or in combination with the anchors, for derivatizing said proteins.

H. Implementation of the Method of the Invention for Preparing (S)-alkanols

The enzymes with dehydrogenase activity which are used according to the invention may be used as free or immobilized enzymes in the process of the invention.

The process of the invention is advantageously carried out at a temperature between 0° C. to 95° C., preferably between 10° C. to 85° C., particularly preferably between 15° C. to 75° C.

In the process of the invention, the pH is advantageously kept between pH 4 and 12, preferably between pH 4.5 and 9, particularly preferably between pH 5 and 8.

In the process of the invention, enantiomerically pure or chiral products or optically active alcohols mean enantiomers which exhibit enantiomer enrichment. Enantiomeric purities of at least 70% ee, preferably of at least 80% ee, particularly preferably of at least 90% ee, very particularly preferably of at least 98% ee, are preferably achieved in the process.

It is possible to use for the process of the invention growing cells which comprise the nucleic acids, nucleic acid constructs or vectors of the invention. It is also possible to use resting or disrupted cells. Disrupted cells mean, for example, cells which have been made permeable by way of treatment with solvents, for example, or cells which have been broken up by way of treatment with enzymes, by way of mechanical treatment (e.g. French press or ultrasonication) or by way of another method. The crude extracts obtained in this manner are advantageously suitable for the process of the invention. It is also possible to use purified or partially purified enzymes for the process. Immobilized microorganisms or enzymes which may advantageously be applied in the reaction are likewise suitable.

Free organisms or enzymes are, when used for the process of the invention, conveniently removed prior to extraction, for example via filtration or centrifugation.

The product produced in the process of the invention, for example (1S)-3-methylamino-1-(2-thienyl)propan-1-ol can advantageously be obtained from the aqueous reaction solution by way of extraction or distillation. For the purpose of increasing the yield, the extraction may be repeated several times. Examples of suitable extractants are solvents such as toluene, methylene chloride, butyl acetate, diisopropyl ether, benzene, MTBE or ethyl acetate, without being limited thereto.

After concentrating the organic phase, the products can usually be obtained with good chemical purities, i.e. more than 80% chemical purity. After extraction, the organic phase containing the product may, however, also be concentrated only partially and the product may be crystallized out. For this purpose, the solution is advantageously cooled to a temperature of from 0° C. to 10° C. The crystallization may also be carried out directly from the organic solution or from an aqueous solution. The crystallized product may be taken up again in the same or in a different solvent for the purpose of renewed crystallization and recrystallized. The subsequent advantageous crystallization which is carried out at least once may, if necessary, further increase the enantiomeric purity of the product.

The work-up types mentioned enable the product of the process of the invention to be isolated with yields of from 60 to 100%, preferably from 80 to 100%, particularly preferably from 90 to 100%, based on the substrate used for the reaction, such as, for example, 3-methylamino-1-(2-thienyl)propan-1-one. The isolated product is characterized by a high chemical purity of >90%, preferably >95%, particularly preferably of >98%. The products furthermore have high enantiomeric purity which can advantageously be increased further by the crystallization, if necessary.

The process of the invention can be operated batchwise, semi-batchwise or continuously.

The process may advantageously be carried out in bioreactors as described, for example, in Biotechnology, volume 3, 2nd edition, Rehm et al. Eds., (1993), in particular chapter II.

The description above and the examples below serve only to illustrate the invention. The invention likewise comprises the numerous possible modifications which are obvious to the skilled worker.

EXPERIMENTAL PART

Example 1

Analysis of 3-chloro-1-(thien-2-yl)propan-1-one and 3-chloro-1-(thien-2-yl)propan-1-ol The concentrations of 3-chloro-1-(thien-2-yl)propan-1-one and 3-chloro-1-(thien-2-yl)propan-1-ol can be determined by means of HPLC. It is also possible, depending on the choice of stationary and mobile phases, to determine the ee value in addition to the concentration.

a) Achiral Analysis

The reaction was quantified using the following system:

| | |
|---|---|
| Stationary phase: | Chromoltih SpeedROD RP18, 50 * 4, 6 μm, Merck (Darmstadt, Germany), heated to 45° C. |
| Mobile phase: | Eluent A: 10 mM $KH_2PO_4$, pH 2.5 |
| | Eluent B: acetonitrile |
| | Gradient: 0-0.5 min, 35% B; 0.5-1.0 min 35 to 80% B; 1.0-1.2 min |
| | 80% B; 1.2-1.3 min 80%-35% B; 1.3-2.0 min 35% B; |
| Flow rate: | 1.5 ml/min |
| Detection: | UV detection at 230 and 260 nm |
| Retention times: | 3-chloro-1-(thien-2-yl)propan-1-one: approx. 1.6 min |
| | 3-chloro-1-(thien-2-yl)propan-1-ol: approx. 1.3 min |

Using authentic material, a calibration series is produced, on the basis of which the concentration of unknown samples can be determined.

b) Chiral Analysis

| | |
|---|---|
| Stationary phase: | Chiracel OD-H, 250 * 4, 6 μm, Daicel, heated to 40° C. |
| Mobile phase: | Eluent A: n-hexane |
| | Eluent B: isopropanol |
| | isocratic with 2.5% B |
| Flow rate: | 1.0 ml/min |
| Detection: | UV detection at 230 and 260 nm |
| Retention times: | 3-chloro-1-(thien-2-yl)propan-1-one: approx. 9.5 min |
| | (1S)-3-chloro-1-(thien-2-yl)propan-1-ol: approx. 16.6 min |
| | (1R)-3-chloro-1-(thien-2-yl)propan-1-ol: approx. 18.3 min |

Example 2

Provision of Glucose Dehydrogenase for Cofactor Regeneration

Glucose dehydrogenase may be used for cofactor regeneration. The enzyme can be obtained from commercial sources (e.g. Jülich Fine Chemicals Order No. 22.10 or 19.10) or else may readily be prepared based on the known DNA sequence. An *E. coli* XL10 Gold clone which comprises the *Bacillus subtilis* glucose dehydrogenase gene (Genbank Acc. No. M12276) in the pUC19 plasmid was used; this construct is referred to as *E. coli* LU11293.

The following medium was prepared for fermentation of *E. coli* LU11293:

| | |
|---|---|
| 560 g | Yeast extract (65%) |
| 448 g | Trypton (Difco) |
| 42 g | $KH_2PO_4$ |
| 84 g | $Na_2HPO_4$ |
| 644 g | Glycerol (99%) |
| 100 ml | SL4 solution (5×) |
| 1 g | Tegosipon 3062 |
| | Dilute medium with water to 13.5 l, adjust pH to 7.0, remove approx. 300 ml for preculture, then sterilize at 122° C. for 30 min. |
| | Add sterile salt solution* (remove the salt solution for the shaker flasks beforehand, see protocol). |

*Salt solution:

| | |
|---|---|
| 2.1 g | $CaCl_2 * 2H_2O$ |
| 3.5 g | $MgSO_4 * 7H_2O$ |
| 14 g | $NH_4Cl$ |
| 14 ml | Ampicillin solution (100 mg/ml) |
| | Dissolve in 500 ml of water and sterilize by filtration. |

In each case 150 ml of medium were sterilized in two 1 l Erlenmeyer flasks and completed with 5 ml of sterile salt solution. After inoculating from an LB ampicillin agar plate, the precultures were incubated at 37° C. and 200 rpm for 12 hours and added to the fermentation medium. The fermentation was started at 37° C., 0.1 bar of internal pressure, pH 7.0 (regulation with 20% phosphoric acid and 25% NaOH), with a gassing rate of 7.5 l/min and 300 rpm (regulation of $pO_2$ between 20 and 50% with 10-20 l/min inlet air and 500-1500 rpm). After 2 h, 0.1 mM IPTG was added for induction and the fermentation was stopped after a total time of 13 h. After harvesting and washing the cells (1.3 kg), the latter were stored at −20° C. until use (2-20 g/l in the reaction mixture).

Example 3

Cofactor Regeneration

The cofactor may also be regenerated by the dehydrogenase which causes the conversion of alkanones (II) to alkanols (I). In this case, addition of a separate regeneration enzyme is not required. The dehydrogenase accepts various monohydric alcohols as reducing agents. They are oxidized to the corresponding carbonyl compounds. A monohydric alcohol which is suitable for regenerating NADH with dehydrogenase is isopropanol. 10% isopropanol is used instead of glucose dehydrogenase and glucose in the reaction mixture.

We claim:

1. A process for preparing an optically active alkanol of formula I

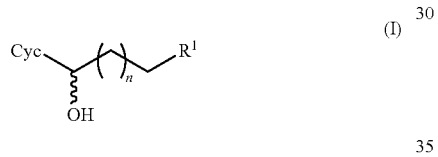
(I)

wherein n is an integer from 0 to 5;

Cyc is an optionally substituted, mono- or polynuclear, saturated or unsaturated, carbocyclic or heterocyclic ring; and $R^1$ is a halogen, SH, OH, $NO_2$, $NR^2R^3$ or $NR^2R^3R^{4+}X^-$, wherein $R^2$, $R^3$ and $R^4$ independently are hydrogen or a lower alkyl or lower alkoxy radical, and $X^-$ is a counterion comprising incubating the alkanone of formula II

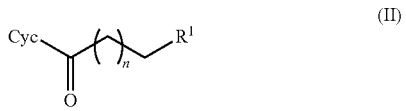
(II)

in which n, Cyc and $R^1$ are as defined above,
in a medium comprising
(i) an enzyme comprising the amino acid sequence of SEQ ID NO: 1, or
(ii) an enzyme comprising an amino acid sequence having at least 95% identity to the amino acid sequence of SEQ ID NO:1, and wherein the enzyme retains at least 50% of the dehydrogenase activity of the enzyme comprising the amino acid sequence of SEQ ID NO:1, wherein the alkanone of formula II is enzymatically reduced to the compound of formula I;
and isolating the product formed.

2. The process of claim 1, wherein the optically active alkanol of formula I is a 1-(2-thienyl)-(S)-propanol of formula III,

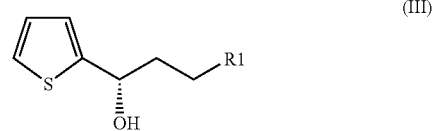
(III)

wherein $R^1$ is Cl or $NHCH_3$, the alkanone of formula II is a 1-(2-thienyl)propanone of formula IV

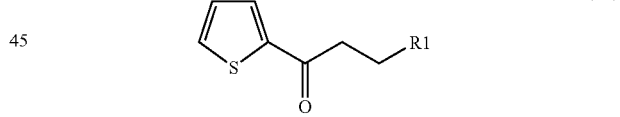
(IV)

wherein $R^1$ is as defined above,
and the isolated product is essentially enantiomerically pure.

3. The process of claim 1, wherein the enzyme is isolated from a microorganism of the genus *Lactobacillus*.

4. The process of claim 1, wherein the incubation further comprises adding reduction equivalents or regenerating reduction equivalents consumed in the reaction.

5. The process of claim 4, further comprising regenerating cofactors with a $C_2$-$C_{10}$-alkanol.

6. The process of claim 1, wherein the medium comprises a microorganism that has been transformed with a nucleic acid construct encoding an enzyme comprising
(i) the amino acid sequence of SEQ ID NO: 1, or
(ii) an amino acid sequence having at least 95% identity to the amino acid sequence of SEQ ID NO:1, and wherein the enzyme retains at least 50% of the dehydrogenase activity of the enzyme comprising the amino acid sequence of SEQ ID NO:1.

7. An isolated enzyme having dehydrogenase activity comprising
(i) the amino acid sequence of SEQ ID NO: 1, or
(ii) an amino acid sequence having at least 95% identity to the amino acid sequence of SEQ ID NO:1, and wherein the enzyme retains at least 50% of the dehydrogenase activity of the enzyme comprising the amino acid sequence of SEQ ID NO:1.

8. A method for preparing an optically active alkanol of formula I

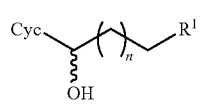

wherein n is an integer from 0 to 5;
Cyc is an optionally substituted, mono- or polynuclear, saturated or unsaturated, carbocyclic or heterocyclic ring; and
$R^1$ is a halogen, SH, OH, $NO_2$, $NR^2R^3$ or $NR^2R^3R^{4+}X^-$, wherein $R^2$, $R^3$ and $R^4$ independently are hydrogen or a lower alkyl or lower alkoxy radical, and $X^-$ is a counterion or an optically active alkanol of formula III

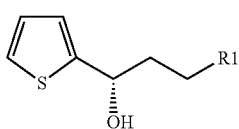

wherein $R^1$ is Cl or $NHCH_3$, comprising incubating the alkanone of formula II

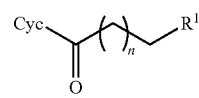

in which n, Cyc and $R^1$ are as defined for formula I above,
or the alkanone of formula IV

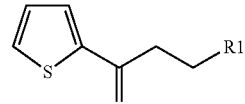

in which $R^1$ is as defined for formula III above, with the enzyme of claim 7.

9. The method of claim 8, further comprising additional conversion of the optically active alkanol of formula I to duloxetine.

10. The process of claim 6, wherein the microorganism is selected from the group consisting of the bacterial families Enterobacteriaceae, Pseudomonadaceae, Rhizobiaceae, Streptomycetaceae and Nocardiaceae.

* * * * *

SEQUENCE LISTING

```
<160> NUMBER OF SEQ ID NOS: 1

<210> SEQ ID NO 1
<211> LENGTH: 249
<212> TYPE: PRT
<213> ORGANISM: Lactobacillus brevis

<400> SEQUENCE: 1

Met Thr Asp Arg Leu Lys Asp Lys Val Ala Ile Ile Thr Gly Gly Val
1               5                   10                  15

Ala Gly Ile Gly Leu Gly Ile Ala Glu Cys Tyr Val Arg Glu Gly Ala
            20                  25                  30

Lys Val Val Val Thr Ala Asn His Asn Val Asp Gly Gly His Ala Ala
        35                  40                  45

Val Ala Lys Phe Gly Asp Asp Val Ser Leu Phe Val Gln Gln Asp Val
    50                  55                  60

Ser Lys Glu Ala Asp Trp Gln Lys Val Ile Asp Ala Thr Ile Ala Lys
65                  70                  75                  80

Phe Gly Arg Val Asp Ile Leu Val Asn Asn Ala Gly Ile Gly Gly Val
                85                  90                  95

Asn Thr Ala Ile Glu Asp Leu Asp Leu Ala Asp Trp Gln Lys Val Ile
            100                 105                 110

Asp Val Asn Leu Thr Ala Asn Phe Leu Gly Glu Lys Ala Ala Ile Lys
        115                 120                 125
```

```
Ala Met Lys Gln Thr Ala Asp Ala Lys Gly Ser Ile Ile Asn Val Ser
    130             135             140

Ser Val Ala Gly Leu Val Gly Leu Pro Met Ala Pro Ala Tyr Ser Ala
145             150             155             160

Ser Lys Gly Gly Ser Arg Leu Leu Thr His Ala Thr Ala Leu Asn Leu
                165             170             175

Ala Gln Arg Gly Ile Asp Ile Arg Val Asn Ser Val His Pro Gly Trp
            180             185             190

Ile Asp Thr Ser Ile Val Pro Glu Ala Ala Arg Gln Gln Ile Ile Ala
        195             200             205

Thr Ile Pro Val Gly His Met Gly Gln Pro Gln Asp Ile Gly Glu Ile
    210             215             220

Cys Val Tyr Leu Gly Ser Asp Glu Ser Arg Phe Ala Asn Gly Ala Glu
225             230             235             240

Phe Thr Val Asp Gly Gly Gln Arg Ala
                245
```